United States Patent [19]

Devic

[11] Patent Number: 5,480,788
[45] Date of Patent: Jan. 2, 1996

[54] BLEACHING OF PLANT MATERIALS

[75] Inventor: Michel Devic, Ste Foy les Lyon, France

[73] Assignee: Elf Atochem S.A., La Defense, France

[21] Appl. No.: 277,948

[22] Filed: Jul. 19, 1994

Related U.S. Application Data

[63] Continuation of Ser. No. 850,312, Mar. 12, 1992, abandoned.

[30] Foreign Application Priority Data

Mar. 15, 1991 [FR] France ................... 91 03177

[51] Int. Cl.$^6$ ............... C12P 3/00; D21C 1/00; A21D 2/04
[52] U.S. Cl. .............. 435/168; 435/277; 426/261; 426/254
[58] Field of Search .................. 435/267, 277, 435/168; 426/253, 261, 254

[56] References Cited

U.S. PATENT DOCUMENTS

| | | | |
|---|---|---|---|
| 4,241,093 | 12/1980 | Farag et al. | 426/258 |
| 4,246,289 | 1/1981 | Tu | 426/254 |
| 4,416,982 | 11/1983 | Tsuda et al. | 435/11 |
| 4,649,113 | 3/1987 | Gould | 435/165 |
| 4,844,924 | 7/1989 | Stanley | 426/258 |
| 5,094,866 | 3/1992 | Devic | 426/261 |
| 5,124,171 | 6/1992 | Devic | 426/640 |
| 5,219,601 | 6/1993 | Devic | 426/254 |

FOREIGN PATENT DOCUMENTS

| | | |
|---|---|---|
| 0402280 | 11/1990 | European Pat. Off. . |
| 2392866 | 10/1978 | France . |
| 53-47563 | 10/1976 | Japan . |
| 54-140761 | 11/1979 | Japan . |

OTHER PUBLICATIONS

English translation of Japanese Kokai 54–140761 (Application 53–47563), (1976).

Primary Examiner—William H. Beisner
Assistant Examiner—T. J. Reardon
Attorney, Agent, or Firm—Burns, Doane, Swecker & Mathis

[57] ABSTRACT

A variety of plant materials adopted for processing into, e.g., low-calorie vegetable fibers and dietary flours, are bleached by (1) soaking a plant material having a moisture content of up to 50% at a temperature ranging from 20° to 100° C. with an aqueous solution containing an alkaline agent and more than 100 g/l of hydrogen peroxide, and having a pH of at least 8.5, such that the aqueous solution is completely absorbed by the plant material without establishing any liquid phase; (2) heating the soaked plant material at a temperature ranging from 40° to 100° C. for a period of time sufficient to effect the bleaching, and washing the bleached plant material with water and drying it.

17 Claims, No Drawings

BLEACHING OF PLANT MATERIALS

This application is a continuation of application Ser. No. 07/850,312, filed Mar. 12, 1992, now abandoned.

CROSS-REFERENCE TO COMPANION APPLICATION

My application Ser. No. 07/850,127 now U.S. Pat. No. 5,219,601, filed concurrently herewith and assigned to the assignee hereof.

BACKGROUND OF THE INVENTION

1. Field of the Invention

The present invention relates to the bleaching of plant materials, more particularly plant materials destined for nutritional consumption, by means of hydrogen peroxide in an aqueous alkaline solution to enhance the whiteness thereof.

The plant materials which can be bleached according to the invention include all products of vegetable origin, which are used for nutrition, either in their entirety or parts thereof. Exemplary such products are cereal grains (wheat, maize, oats, barley, rice, etc.), peels, skins, pips of fruits, bran from oil plants, such as sunflowers, bran from cereals; it is also envisaged to bleach residues of various products such as beet or sugar beet, fruits such as pears, peaches, apples, apricots, grapes, oil plants, such as sunflowers, soya bean, citrus fruit such as lemon, cereals, residues resulting from extracting the fraction of these products which normally enhances their value, namely, sugar, fruit juice, pectin, oil or starch. It is also envisaged to bleach residues of fruit and cereals after alcoholic fermentation (grape malt, residues from alcoholic distillation, etc.) or almond shells, or shells of nuts with or without the fruit.

2. Description of the Prior Art

Plant materials of the above type are typically treated with aqueous alkaline solutions which contain hydrogen peroxide to "delignify" and bleach them.

Such bleached plant materials have a high plant fiber content and can be used, especially, for producing edible food products and, in particular, low-calorie food products, for example dietary flours.

However, the food products obtained from these fibers are too dark in color to permit them to be used as flour substitutes.

The known processes for converting plant materials into products which have a high cellulosic vegetable fiber content and which, moreover, have a whiteness suitable for commercial use, are generally processes carried out in aqueous medium. Thus, U.S. Pat. No. 4,649,113 to Gould describes the treatment of various vegetable fibers with $H_2O_2$ in an alkaline medium. The dietary fibers are suspended in water in amounts ranging from 20 to 300 g/l in such manner that they are completely wet, then $H_2O_2$ and NaOH are added, and the action of $H_2O_2$ occurs in an aqueous medium.

FR-A-2,647,641 and EP-A-337,653, for example, describe treating the plant materials prior to the bleaching step with an acid or basic solution, such as to improve, notably, the whiteness thereof. Each of these processes is carried out in an aqueous medium.

These bleaching processes present disadvantages because it is necessary for them to be carried out in an aqueous medium. Thus, the cereal-derived dietary fibers, such as wheat bran, maize bran, etc., always contain a substantial amount of flour or starch and, when wetted, form very viscous "pastes" which are very difficult to stir and to manipulate. The bleaching medium must therefore be highly diluted.

Moreover, the dietary fibers which have a very high water retention capacity, such as, for example, beet pulp, increase up to 10-fold in volume and weight. This reduces the productivity of the processing apparatus.

Finally, the diffusion of the reactants into the dietary fibers requires a lengthy period of time and necessitates either high-performance and very expensive stirrers/mixers, or long reaction times in a highly diluted medium with traditional stirring.

FR-A-2,651,965 describes a process for bleaching vegetable fiber in which the vegetable fiber, which has a consistency of greater than or equivalent to 10% (namely, a moisture content <90%), preferably ranging from 20% to 35% (namely, a moisture content ranging from 65% to 80%), is soaked with an alkaline aqueous hydrogen peroxide solution and bleached during drying.

This process enables a bleached dry fiber to be obtained whose degree of whiteness is superior to the traditional processes in a liquid medium, but which, on the other hand, present another shortcoming: the bleaching and dried fiber contains a variable amount of residual hydrogen peroxide which originates from the incomplete reaction of $H_2O_2$ during the drying step.

SUMMARY OF THE INVENTION

Accordingly, a major object of the present invention is the provision of an improved process for bleaching plant materials which avoids or conspicuously ameliorates the above disadvantages and drawbacks to date characterizing the state of the art and which can be carried out under dry conditions permitting the elimination of residual peroxides, to obtain vegetable fibers having a very high degree of whiteness which can be used for nutrition, i.e., for the production of edible comestibles.

Briefly, the present invention features the bleaching of plant material via treatment with an alkaline aqueous hydrogen peroxide solution, comprising:

(a) heating a plant material substrate, which has a moisture level of less than or equivalent to 50% at a temperature ranging from 40° to 100° C., (b) soaking the plant material obtained in step (a) with an alkaline aqueous hydrogen peroxide solution having a pH greater than or equivalent to 8.5 and which contains more than 100 g/l of peroxide, at a temperature ranging from 20° C. to 100° C. such that all of the solution is absorbed by the plant material, (c) heating the material which has thus been soaked at a temperature ranging from 40° C. to 100° C. during the period of time required for bleaching the material, (d) washing the bleaching plant material obtained in step (c) with water, and (e) drying such washed material.

DETAILED DESCRIPTION OF THE PREFERRED EMBODIMENTS OF THE INVENTION

More particularly according to the present invention, the plant materials which can be treated can be those indicated above, namely, especially, whole grains of cereals, brans of oil plants, of cereals or those residues obtained after extracting the portion which enhances their value from materials such as beet, citrus fruit, fruit, oil plants or cereals.

The process according to the invention is characterized in that the fiber is bleached in a dry environment, namely, without apparent liquid phase. The initial moisture content before soaking with the alkaline aqueous hydrogen peroxide solution is selected to be low enough to permit complete and rapid absorption of such alkaline solution.

This limit principally depends on the water absorption capacity of the fiber and on the volume of alkaline aqueous hydrogen peroxide solution.

A moisture content of less than 50% permits virtually all plant materials such as described above to be bleached in a dry environment. In general, the initial moisture content must be as low as possible and preferably less than 20%. In particular, this moisture content advantageously ranges from 4% to 40% in the case of plant pulps originating from, for example, sugar beet and extracted fruit pulps, and from 1% to 5% in the case of materials derived from cereals such as bran of wheat, maize, sunflowers or oats.

Before the heating phase (step a) of the process according to the invention, it may be necessary to dry the plant material such that it has the desired moisture level.

Drying is effected by the customary means of drying which are suitable for the material to be treated such as, for example, hot-air dryers, vapor dryers or vacuum dryers. The drying temperature advantageously ranges from 40° to 160° C., depending on the particular technique employed.

Even though the process according to the invention is more effective, the lower the initial moisture content of the fiber, such content is frequently maintained above a minimum ranging from 4% to 11%, depending on the fibers, for safety reasons due to the danger of flammability of the flours and dust.

Most of the materials derived from cereals have a natural moisture content of less than 20% and therefore do not have to be dried first.

The dried starting material can be treated as is, or else after a more or less fine grinding. A coarse grinding to a particle size of 0.5 to 2 mm is preferably carried out to facilitate stirring and soaking.

After this possible drying phase, the plant material to be treated which has the desired moisture level is heated at a temperature ranging from 40° C. to 100° C. and, preferably, from 70° C. to 95° C. The duration of this heating step is generally less than 2 hours and, preferably, ranges from 10 minutes to 60 minutes, depending on the nature of the fibrous material.

The heating phase (a) of the process according to the invention permits, especially, the effectiveness of the bleaching process to be improved.

The subsequent phase (b) of the process comprises soaking the material to be treated with an aqueous alkaline hydrogen peroxide solution. This soaking must be complete, namely, all of the alkaline solution must be absorbed by the material, and no aqueous phase must remain in contact with the plant material.

The aqueous alkaline hydrogen peroxide solution contains more than 100 g/l of peroxide and has a pH of greater than or equivalent to 8.5.

The hydrogen peroxide is typically used in the form of an aqueous solution of 30% to 70% strength. The commercial solution of 35% strength hydrogen peroxide, food quality, is preferably used.

The amount of hydrogen peroxide used advantageously varies from 1% to 20% by weight relative to the dry weight of the material, depending on the desired degree of whiteness and depending on the nature of the fibrous material. In general, an amount of 5% to 10% by weight of hydrogen peroxide enables satisfactory bleaching.

All alkaline agents, either alone or as a mixture, which permit the hydrogen peroxide solution to be adjusted to a pH of greater than or equivalent to 8.5 can be used. Exemplary thereof are sodium hydroxide, potassium hydroxide, sodium carbonate, potassium carbonate, calcium oxide CaO and magnesia MgO.

The alkaline agent is typically used in the form of a 10% to 20% strength aqueous solution. The preferred alkaline agent is sodium hydroxide in a 10% strength aqueous solution.

The amount of alkaline agent used, expressed as NaOH relative to the dry weight of the plant material to be treated, varies depending on the nature of the material and the amount of peroxide used. It typically ranges from 0.5% to 10% and, more particularly, from 1% to 4%. The maximum amount is preferably such that the pH of the material after bleaching is less than or equivalent to 8.5 in the case of most materials.

Finally, the amount of solution of alkaline agent must be such that, after mixing with the peroxide, the alkaline $H_2O_2$ solution has a concentration greater than or equivalent to 100 g of peroxide per liter.

In certain instances, it can be advantageous to add, in an amount of less than or equivalent to 5% by weight relative to the dry weight of the material to be treated, hydrogen peroxide stabilizers and/or complexing or sequestering agents for metal ions, these agents being suitable/compatible for the production of edible comestibles, for example sodium silicate, soluble magnesium salts, citric acid, sodium tripolyphosphate, and pyrophosphoric acids.

However, in a preferred embodiment of the invention for producing fibers for dietary use, no additive whatsoever is added to the alkaline hydrogen peroxide solution.

The bleaching treatment according to the invention must be carried out in a dry environment in the solid state.

The amounts and concentrations of the reactants of the alkaline aqueous hydrogen peroxide solution must thus be selected such that all of the solution is absorbed by the plant material over the course of the soaking.

All means which permit rapid, homogeneous soaking of the dry material to be treated, typically in the form of a powder, with the alkaline peroxide solution can be used, for example powder mixers, kneaders, extruder screws, rotating drums, and the like.

The alkaline peroxide solution is typically introduced continuously and distributed uniformly. In a preferred embodiment of the invention, the alkaline peroxide solution is continuously sprayed onto the powdered plant material in a mixer-disperser.

The temperature during the soaking phase advantageously ranges from 20° to 100° C. and, preferably, from 60° to 90° C.

During the soaking step, it may be necessary to cool or heat the plant material to maintain the temperature at the selected level.

The soaking time is selected depending on the capacities of the apparatus to ensure homogeneous mixing and to maintain the desired temperature. In general, a soaking time of from a few minutes to a few hours is required, depending on the type of apparatus used.

After the phase in which the plant material to be treated is soaked with the alkaline hydrogen peroxide solution, the temperature of the plant material is maintained at from 40° to 100° C. and, preferably, from 50° to 90° C. (phase c).

The heating time depends on the nature of the material and the amount of peroxide; too long a heating time can, however, effect a decline in the whiteness value. In general, the heating time ranges from 10 minutes to several hours for most materials, and it typically ranges from 1 to 2 hours for a temperature of 80° C. The pH of the medium decreases while the soaked material is heated.

It is advantageous for the treatment of most plant materials to select an amount of alkaline agent, a heating time and a temperature such that when the bleaching is completed, the pH of the medium is around neutrality and at most equivalent to 8.5. This eliminates the necessity of a subsequent neutralization treatment with an acid.

After the bleaching step, the fibrous material is washed once or more than once with water in an amount sufficient to eliminate the residual peroxide and reduce the mineral matter to the desired level.

The washing step can be carried out with optionally demineralized water at a temperature of from 20° to 100° C. Washing can be effected by dilution with water followed by separation of the liquid phase by means of a filter or a press, or else by directly passing the water through the fibrous material which is arranged on a filter or in a press.

Upon completion of the washing step, the plant material is dried to the moisture content required for its use or its conversion into flour.

Drying is effected by the customary techniques suited to each plant material.

The drying temperature and drying time are selected in such manner as to avoid yellowing of the fiber during the drying operation.

To the process steps according to the invention, there may be added a treatment step in which the bleached plant material is treated with an enzyme such as catalase which is capable of decomposing peroxide.

This step can be carried out after the washing step, or else during this step.

Such enzyme treatment is carried out by soaking the bleached material at a temperature from 20° C. to 50° C. with an aqueous catalase solution for a treatment time ranging from a few minutes to several hours, depending on the nature of the fiber and the temperature.

The treatment time preferably ranges from 10 minutes to 2 hours at a temperature of from 25° to 45° C. The treatment can be carried out in an aqueous medium at a strength of 2% to 40%.

The catalase used can be animal derived, such as the catalase extracted from bovine liver, or else it can originate from mold cultures, such as *Aspergillus niger*.

The amount used is calculated as a function of the amount of residual peroxide and the activity of the catalase used.

A washing step can be carried out after the catalase treatment.

The process according to the invention presents a series of advantages. In particular, the dry treatment of the plant materials allows a higher degree of whiteness to be attained with the same amount of hydrogen peroxide. It has also been observed that the process reduces the degradation of the components of the plant material, due to the fact that the bleaching is conducted at the surface of the fibers, the materials to be treated not being wetted by the aqueous phase.

Moreover, the process according to the invention permits heating energy to be saved because it is carried out in a dry environment; in addition, the apparatus used for the bleaching process can be simpler (treatment of dry materials) and has a higher productivity.

In order to further illustrate the present invention and the advantages thereof, the following specific examples are given, it being understood that same are intended only as illustrative and in nowise limitative.

In said examples to follow, the amounts of reactants are expressed in percentages by weight relative to the dry plant material to be treated.

Also in said examples to follow, the degree of whiteness of the plant material before or after the bleaching step was measured by means of a reflectometer at 457 nm, following the ISO standard for paper industry, and is expressed in ISO degrees.

EXAMPLE 1

176.2 g of fresh beet pulp obtained after the sugar had been extracted, having a water content of 77.3%, were dried in an oven at 80° C. until a moisture content of 20% was obtained, i.e., a weight of 50 g (40 g dry weight).

The powdered pulp which had a moisture content of 20% was then placed in a 1 l mixing reaction vessel and heated at 70° C. for 30 minutes. 19.45 g of an alkaline $H_2O_2$ solution composed of 11.45 g of 35% strength $H_2O_2$ solution (i.e., 10% of $H_2O_2$ by weight) and 8 g of 10% strength sodium hydroxide (i.e., 2% of NaOH) was then sprayed thereon. This solution had a pH of 9.9 and contained 200 g of $H_2O_2$/l. The soaking time was 4 minutes and the temperature was maintained at 70° C.

The powder was stirred for 1 hour at 70° C.; the pH of the bleached fiber was then 5.8. The powder was then suspended in 600 cm³ of water at 50° C., and 50 mg of catalase at 274,000 U/ml were added. After 15 minutes at 50° C., the mixture was filtered and dried at 70° C. in the oven.

This provided 33.8 g of bleached dry pulp having a whiteness of 40.1° ISO, a pH of 5.9 and a residual $H_2O_2$ content of less than 10 ppm.

The whiteness of the untreated pulp was 31.5° ISO.

EXAMPLE 2

The procedure of Example 1 was repeated, except that the initial drying of the beet pulp was carried out up to a moisture content of 40%, i.e., a weight of 66.5 g (40 g dry weight).

This provided 32 g of bleached dry pulp having a whiteness of 39.6° ISO, a pH of 5.7 and a residual $H_2O_2$ content of less than 10 ppm.

EXAMPLE 3 (Comparative)

The procedure of Example 1 was repeated, except that the initial drying of the beet pulp was carried out up to a moisture content of 60%, i.e., a weight of 100 g (40 g dry weight).

This provided 34 g of bleached dry pulp having a whiteness of 37.2° ISO and a pH of 5.8.

EXAMPLE 4 (Comparative)

The procedure of Example 1 was repeated, but without initial drying of the beet pulp, which was used at a moisture content of 77.3%.

The whiteness obtained was 36.5° ISO and the pH was 5.9.

Examples 3 and 4 demonstrate that, if bleaching was not carried out under the conditions of the process according to the invention, especially as regards the moisture content, then the degree of whiteness obtained was lower than that obtained with the same amounts of reactant, but with a moisture content of the pulp, before soaking, of less than 50%.

EXAMPLE 5

A 100 l stainless steel mixing reaction vessel was charged with 10.42 kg of dried beet pulp (after the sugar had been extracted) having a moisture content of 4.2% and being ground coarsely (0.5 to 1 mm), i.e., a dry weight of 10 kg.

The powder was heated for 15 minutes at 70° C. with stirring. Onto the stirred powder were sprayed 4.86 kg of an alkaline $H_2O_2$ solution consisting of 2.86 kg of 35% strength $H_2O_2$ and 2 kg of 10% strength NaOH. This solution had a pH of 9.9 and contained 200 g/l of $H_2O_2$.

The soaking time was 20 minutes and the temperature of the powder was 88° C. during soaking.

The powder was then heated for 1 hour at 70° C. The pH of the fiber was then 5.9. The powder was suspended in 80 l of water, filtered, and washed with 100 l of cold water.

The washed pulp was then dried for 12 hours at 60° C. to a moisture content of 5%. This provided 9.49 kg of bleached beet pulp having a pH of 6.3 and a whiteness of 38.5° ISO. The whiteness of the pulp before treatment was 30.5° ISO.

EXAMPLE 6

A 100 l stainless steel mixing reaction vessel was charged with 20 kg of ground maize bran having a moisture content of 8% (18.4 kg dry weight).

The powder was heated for 15 minutes at 70° C., and then 8.93 kg of an alkaline $H_2O_2$ solution consisting of 6.165 kg of 30% strength $H_2O_2$ and 2.77 kg of 10% strength NaOH, i.e., a solution containing 200 g of $H_2O_2$/l and a pH of 9.5, was sprayed thereon.

The soaking time was 1 hour, and the temperature of the powder during soaking was 90° C. Stirring was continued for 15 minutes at 90° C. The bleached maize bran was then washed with 180 l of water, at 20° C., and dried in vacuo for 3 hours at 90° C.

This provided 17 kg of bleached bran having a moisture content of 7.1% and a pH of 8, a residual $H_2O_2$ content of less than 20 ppm and a whiteness of 43° ISO. The whiteness of the untreated bran was 32.8° ISO.

EXAMPLE 7

A 100 l stainless steel mixing reaction vessel was charged with 17.306 kg of dried and ground barley malt which had a moisture content of 8.1% (dry weight 15.9 kg).

The powder was heated for 30 minutes at 95° C., and an alkaline $H_2O_2$ solution composed of 4.54 kg of 35% strength $H_2O_2$ and 2.385 kg of 10% strength NaOH, i.e., a solution containing 230 g of $H_2O_2$/l and having a pH of 9.5, was sprayed thereon.

Soaking was effected at 90° C. for 30 minutes. After soaking, heating was continued for 1 hour at 90° C.; the pH of the powder was then 5.5.

The bleached barley malt was then washed with cold water until peroxide was no longer present in the washing water (the $H_2O_2$ content was less than 2 ppm).

The washed barley malt was then dried at 70° C. This provided 10,753 kg of bleached barley malt having a moisture content of 8%, a pH of 7.1 and a residual $H_2O_2$ content of less than 10 ppm. The whiteness of the bleached fiber was 31° ISO. The untreated fiber had a whiteness of 21.3° ISO.

EXAMPLE 8

103 g of ground sunflower bran having a moisture content of 10% (dry weight 92.7 g) were heated for 10 minutes at 90° C. in a 1 l mixing reaction vessel.

37 g of an alkaline $H_2O_2$ solution consisting of 18.5 g of 35% $H_2O_2$ (i.e., 7% of $H_2O_2$) and 18.5 g of 10% strength NaOH (i.e., 2% of NaOH) were then sprayed thereon.

The soaking time was 7 minutes, and the temperature during soaking was 90° C. The powder was stirred for 30 minutes at 90° C. The pH of the bleached fiber was then 5.5.

The bran powder was then suspended in 500 cm³ of cold water and filtered and then washed with 1 l of water. The sunflower bran was dried to a constant weight in an oven at 80° C.

This provided 84 g of bleached sunflower bran having a pH of 6.9 and a whiteness of 54° ISO.

The starting material bran before treatment had a whiteness of 32.2° ISO.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the bleaching of plant material, comprising (1) soaking a starting plant material having a moisture content of up to 50% at a temperature ranging from 20° to 100° C. with an aqueous solution containing an alkaline agent and more than 100 g/l of hydrogen peroxide, and having a pH of at least 8.5, such that said aqueous solution is essentially completely absorbed by said starting plant material without establishing any liquid phase in contact therewith, and (2) heating the thus soaked plant material at a temperature ranging from 40° to 100° C. for a period of time sufficient to effect the bleaching thereof.

2. The process as defined by claim 1, further comprising washing the bleached plant material with an amount of water sufficient to eliminate residual peroxide and drying said washed, bleached plant material.

3. The process as defined by claim 2, comprising preheating said starting plant material, to achieve moisture content of up to 50%, at a temperature ranging from 40° to 100° C.

4. The process as defined by claim 3, wherein said preheating said starting plant material is conducted for from 10 to 60 minutes.

5. The process as defined by claim 2, comprising washing the bleached plant material with demineralized water or non-demineralized water at a temperature ranging from 20° to 100° C.

6. The process as defined by claim 2, comprising treating the bleached plant material with an enzyme that decomposes hydrogen peroxide either during or subsequent to said washing.

7. The process as defined by claim 1, said starting plant material having a moisture content of less than 20%.

8. The process as defined by claim 1, said starting plant material comprising a sugar beet or fruit pulp having a moisture content ranging from 4% to 40%.

9. The process as defined by claim 1, said starting plant material comprising a cereal product having a moisture content ranging from 1% to 5%.

10. The process as defined by claim 1, said starting plant material having been predried to a moisture content of up to 50% at a temperature ranging from 40° to 160° C.

11. The process as defined by claim 1, said aqueous solution comprising from 1% to 20% by weight of hydrogen peroxide relative to the dry weight of said plant material.

12. The process as defined by claim 11, the aqueous solution alkaline agent comprising from 0.5% to 10% by weight of sodium hydroxide relative to the dry weight of said plant material.

13. The process as defined by claim 1, said aqueous solution comprising at least one hydrogen peroxide stablizing agent and/or at least one complexing or sequestering agent for metal ions.

14. The process as defined by claim 1, comprising heating the soaked plant material for from 10 minutes to several hours.

15. The process as defined by claim 14, comprising heating the soaked plant material for from 1 to 2 hours.

16. The process as defined by claim 1, said starting plant material comprising a particulate edible fiber.

17. The bleached plant material of the process as defined by claim 1.

\* \* \* \* \*